United States Patent
Gao et al.

(10) Patent No.: US 11,944,115 B2
(45) Date of Patent: *Apr. 2, 2024

(54) METHODS AND SYSTEMS FOR INCORPORATING NICOTINE INTO ORAL PRODUCTS

(71) Applicant: Altria Client Services LLC, Richmond, VA (US)

(72) Inventors: Feng Gao, Midlothian, VA (US); Shuzhong Zhuang, Glen Allen, VA (US); Diane L. Gee, Chesterfield, VA (US)

(73) Assignee: Altria Client Services LLC, Richmond, VA (US)

( * ) Notice: Subject to any disclaimer, the term of this patent is extended or adjusted under 35 U.S.C. 154(b) by 240 days.

This patent is subject to a terminal disclaimer.

(21) Appl. No.: 17/380,255

(22) Filed: Jul. 20, 2021

(65) Prior Publication Data
US 2021/0345657 A1 Nov. 11, 2021

Related U.S. Application Data

(60) Continuation of application No. 16/507,243, filed on Jul. 10, 2019, now Pat. No. 11,076,631, which is a
(Continued)

(51) Int. Cl.
*A24B 15/16* (2020.01)
*A23G 4/06* (2006.01)
(Continued)

(52) U.S. Cl.
CPC ............ *A24B 15/16* (2013.01); *A23G 4/06* (2013.01); *A24B 13/00* (2013.01); *A24B 15/285* (2013.01); *A24B 15/303* (2013.01); *C07D 401/04* (2013.01)

(58) Field of Classification Search
None
See application file for complete search history.

(56) References Cited

U.S. PATENT DOCUMENTS 2,162,738 A 6/1939 McCoy
3,139,436 A 6/1964 Bicking
(Continued)

FOREIGN PATENT DOCUMENTS

CN 102754907 A 10/2012
CN 103040090 A 4/2013
(Continued)

OTHER PUBLICATIONS (-) Nicotine, product information sheet, Sigma-Aldrich, [online], retrieved from the Internet, [retrieved Jan. 19, 2016,<URL: http://www.sigmaaldrich.com/catalog/product/sigma/n3876?lang=en&region=US.
(Continued)

*Primary Examiner* — Dennis R Cordray
(74) *Attorney, Agent, or Firm* — Harness, Dickey & Pierce, P.L.C.

(57) ABSTRACT

This document provides methods and systems for stabilizing nicotine and incorporating nicotine into one or more oral products. This document also provides oral products. Nicotine can be stabilized by mixing liquid nicotine with cellulosic fiber such that the liquid nicotine absorbs into pores of the cellulosic fiber to form a cellulosic fiber-nicotine mixture. In some cases, a cellulosic fiber-nicotine mixture can be combined with one or more binders and molded into an oral product.

20 Claims, 1 Drawing Sheet

Related U.S. Application Data division of application No. 15/351,571, filed on Nov. 15, 2016, now Pat. No. 10,349,672, which is a continuation of application No. 14/333,877, filed on Jul. 17, 2014, now Pat. No. 9,521,864.

(60) Provisional application No. 61/856,409, filed on Jul. 19, 2013.

(51) Int. Cl.
*A24B 13/00* (2006.01)
*A24B 15/28* (2006.01)
*A24B 15/30* (2006.01)
*C07D 401/04* (2006.01)

(56) References Cited

U.S. PATENT DOCUMENTS

| | | | |
|---|---|---|---|
| 3,396,735 | A | 8/1968 | Von Bethmann et al. |
| 4,153,063 | A | 5/1979 | Roselius et al. |
| 4,448,208 | A | 5/1984 | Friedrich et al. |
| 4,528,993 | A | 7/1985 | Sensabaugh, Jr. et al. |
| 4,660,577 | A | 4/1987 | Sensabaugh et al. |
| 4,848,373 | A | 7/1989 | Lenkey |
| 5,372,149 | A | 12/1994 | Roth et al. |
| 5,487,792 | A | 1/1996 | King et al. |
| 5,939,100 | A | 8/1999 | Albrechtsen et al. |
| 2002/0059939 | A1 | 5/2002 | Fox |
| 2004/0010787 | A1 | 1/2004 | Traut et al. |
| 2004/0107971 | A1 | 6/2004 | De |
| 2004/0118422 | A1 | 6/2004 | Lundin et al. |
| 2005/0053665 | A1 | 3/2005 | Ek et al. |
| 2005/0178398 | A1 | 8/2005 | Breslin et al. |
| 2007/0269386 | A1* | 11/2007 | Steen ............ A61P 25/00 424/440 |
| 2009/0293895 | A1 | 12/2009 | Axelsson et al. |
| 2010/0004294 | A1 | 1/2010 | Axelsson et al. |
| 2011/0200670 | A1 | 8/2011 | Thakkar |
| 2012/0100194 | A1 | 4/2012 | Yamai et al. |
| 2014/0000634 | A1 | 1/2014 | Mishra et al. |

FOREIGN PATENT DOCUMENTS

| | | |
|---|---|---|
| JP | H9-504305 A | 4/1997 |
| JP | 2002173413 A | 6/2002 |
| JP | 2004527453 A | 9/2004 |
| JP | 2007-505037 A | 3/2007 |
| JP | 2015503930 A | 2/2015 |
| WO | WO-2004/056363 A2 | 7/2004 |
| WO | WO-2004064811 A1 | 8/2004 |
| WO | WO-2007/104574 A2 | 9/2007 |
| WO | WO-2007104573 A2 | 9/2007 |
| WO | WO-2009037319 A2 | 3/2009 |
| WO | WO-2011127182 A1 | 10/2011 |

OTHER PUBLICATIONS

Ethyl Acohol, Pure, product information sheet, Sigma-Aldrich, [online], retrieved from the Internet, [retrieved Jan. 19, 2016,<URL: http:///www.sigmaaldrich.com/catalog/product/sia1/459844?lang=en&region=US>.

Hagiopol et al. Chemistry of Modern Papermaking, CRC Press, p. 52 (2011).

International Preliminary Report on Patentability in International Application No. PCT/US2014/046999, dated Jan. 19, 2016, 7 pages.

International Search Report and Written Opinion in International Application No. PCT/US2014/046999, dated Oct. 27, 2014, 14 pages.

Lovikka et al. "Porosity wood pulp fibers in wet and highly open dry state," Micropor & Mesopor Mtls 234, pp. 326-335, [online], <URL: http://ac.els-cdn.com/S1387181116302931/1-s2.0-S1387181116302931-main.pdf?_tid=635fe703-3884-4179-bea8809f530ab41f&acdnat=1529429417_72982792de4b39da7ddb19aa507f8c58>. (2016).

Japanese Decision of Rejection for Japanese Application No. 2016-527096 dated Dec. 17, 2018, English translation thereof.

European Search Report for Application No. 19194904.9-1105, dated Feb. 3, 2020.

Japanese Notice of Reasons for Rejection for corresponding Application No. 2016-527096, dated May 11, 2020.

European Notice of Opposition for Application No. 14747264.1, dated Jun. 12, 2020.

Avicel PH Binders, FMC BioPolymer, pp. 2-13, retrieved from www.fmcbiopolymer.com, 2005.

Japanese Reasons for Rejection for corresponding Application No. 2019-077104, dated Jul. 29, 2020.

Canadian Office Action for corresponding Application No. 2,918,271 dated Oct. 7, 2020 (4 pages).

European Communication pursuant to Rule 114(2) EPC dated Feb. 2, 2021 for corresponding European Application No. 19194904.9.

European Communication pursuant to Rule 114(2) EPC dated Jan. 21, 2021 for corresponding European Application No. 14747264.1.

European Communication dated Feb. 22, 2021 in corresponding European Application No. 14747264.1 (12 pages).

European Communication regarding Summons to Attend Oral Proceedings Pursuant to Rule 115(1) EPC dated Mar. 31, 2021 in European Application No. 14747264.1 (10 pages).

Canadian Office Action dated Mar. 31, 2021 in corresponding Canadian Application 2918271 (3 pages).

Japanese Office Action for corresponding JP Patent Application No. 2021-018694 dated May 18, 2022, with English language translation (8 pages).

European Office Action for corresponding EP Application 19194904.9 dated Oct. 22, 2021 (5 pages).

Japanese Office Action for corresponding JP Application 2022-158223 dated Aug. 23, 2023, with English language translation (6 pages).

European Notification for EP Application No. 14747264.1 dated Jan. 2, 2024 including Letter of the Opponent dated Dec. 20, 2023 (6 pages).

* cited by examiner

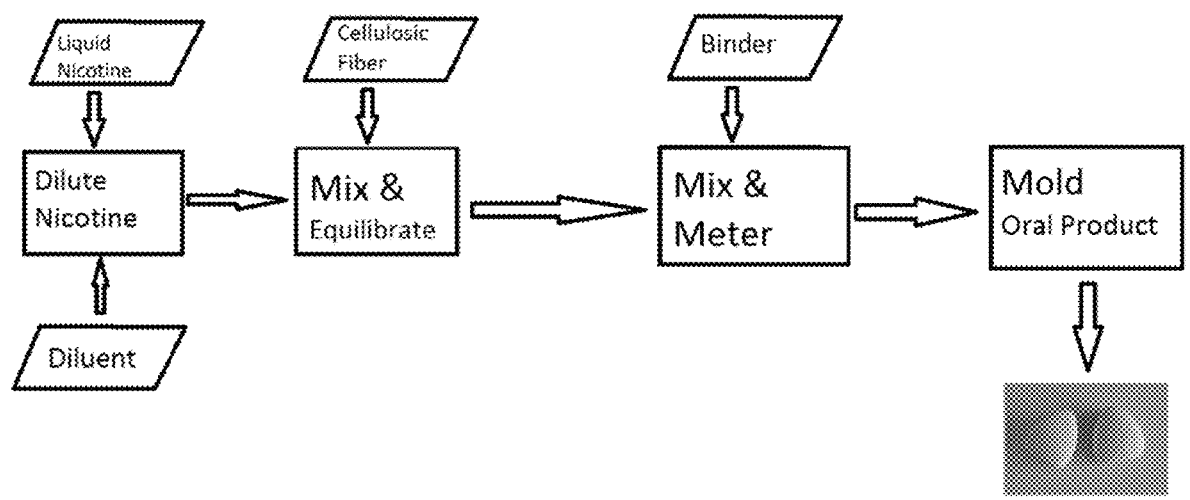

METHODS AND SYSTEMS FOR INCORPORATING NICOTINE INTO ORAL PRODUCTS

CROSS REFERENCE TO RELATED APPLICATIONS

This application is a continuation of U.S. application Ser. No. 16/507,243, filed Jul. 10, 2019, which is a divisional of U.S. patent application Ser. No. 15/351,571, filed Nov. 15, 2016, which is a continuation of U.S. patent application Ser. No. 14/333,877, filed on Jul. 17, 2014, claims benefit under 35 U.S.C. 119(e) to U.S. Application No. 61/856,409, filed on Jul. 19, 2013, the entire contents of each of which are incorporated herein by reference.

TECHNICAL FIELD

This document relates to methods and systems for incorporating nicotine into oral products. For example, methods and systems provided herein can stabilize nicotine for handling and/or incorporation into an oral product.

BACKGROUND

Nicotine is a component of various tobacco products. Over the years, however, various methods and systems have been developed for providing nicotine to adult subjects without the presence of tobacco plant tissue. Some ways tobacco-free nicotine is provided include transdermal patches, lozenges, and nicotine chewing gums.

Nicotine, or 3-(1-methyl-2-pyrrolidinyl) pyridine, is a tertiary amine with the following structure:

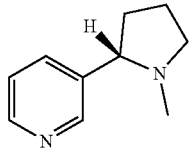

Under ambient conditions, nicotine is an oily, volatile, hygroscopic liquid that is sensitive to light and air. Nicotine's chemical and physical properties present a number of processing and stability issues. For example, because nicotine is volatile, it may evaporate during its incorporation into an oral product such as a gum or lozenge. In an effort to reduce potential processing and stability issues associated with the nicotine compound, a number of nicotine complexes have been developed. For example, one method includes the preparation of a complex of nicotine and an ion exchange resin. A well-known complex that is currently used in the commercially-available nicotine chewing gums is nicotine polacrilex, which is a complex of nicotine and the cation exchange resin AMBERLITE 164.

SUMMARY

This document provides methods and systems for stabilizing nicotine and incorporating liquid nicotine into an oral product. This document provides oral products incorporating liquid nicotine. In some cases, an oral product provided herein can include cellulosic fiber and nicotine absorbed into pores of the cellulosic fiber. In some cases, an oral product provided herein can include a binder matrix, cellulosic fiber within the binder matrix, and nicotine absorbed into pores of the cellulosic fiber. Methods and systems provided herein include mixing liquid nicotine with cellulosic fiber to produce a cellulosic fiber-nicotine mixture. In some cases, the cellulosic fiber-nicotine mixture can be combined with one or more binders and molding the mixture into an oral product having a binder matrix.

Direct incorporation of nicotine into oral products can present a number of difficulties. In some cases, mixing liquid nicotine with a mixture of dry ingredients can disrupt certain molding processes, such as compression molding. In some case, the direct incorporation of liquid nicotine can result in an excessively fast release rate from the resulting oral product. Nicotine complexes, such as nicotine polacrilex, however, can present problems with incorporating nicotine into an oral product. For example, certain molding processes can use temperatures that cause certain nicotine complexes to degrade. In some cases, nicotine complexes can result in an excessively slow release rate of nicotine from the resulting oral product. Moreover, the release rate can be rate limited by chemical reactions that allow the nicotine to be released, thus an adult consumer (e.g., an adult tobacco consumer) can have a limited ability to adjust the release of nicotine. Nicotine complexes sometimes produce acid by-products during the release of nicotine, which can further impede the release of nicotine and/or produce an unpleasant flavor. Some oral products incorporating nicotine complexes can incorporate buffers to control the release rate and/or counteract the release of acid by the nicotine complex, but these buffers can provide unpleasant flavors. For example, sodium carbinate and/or sodium bicarbonate can be used as a buffering agent with a nicotine complex, but sodium carbinate and/or sodium bicarbonate can also provide an undesirable or off-taste.

Combining liquid nicotine with cellulosic fiber as provided herein can provide stabilized nicotine that can be used as an oral product alone or incorporated into oral products. In some cases, oral products provided herein include a binder matrix, cellulosic fiber dispersed in the binder matrix, and nicotine in pores of the cellulosic fiber. The cellulosic fiber-nicotine combination provided herein can be used in a wide variety of molding operations, including compression molding techniques that call for dry ingredients.

Cellulosic fiber used in the methods, systems, and oral products provided herein can be derived from plant tissue. In some cases, cellulosic fiber used in the methods, systems, and oral products provided herein can include cellulose. Cellulosic fibers used in the methods, systems, and oral products provided herein can include lignin and/or lipids. Cellulosic fibers used in the methods, systems, and oral products provided herein can be non-tobacco cellulosic fibers. For example, cellulosic fibers can be selected from the following: sugar beet fiber, wood pulp fiber, cotton fiber, bran fiber, citrus pulp fiber, grass fiber, willow fiber, poplar fiber, and combinations thereof. Cellulosic fiber used in the methods, systems, and oral products provided herein may be chemically treated prior to use. For example, cellulosic fiber used in the methods, systems, and oral products provided herein can be CMC, HPMC, HPC, MCC, or other treated cellulosic material.

Cellulosic fibers used in the methods, systems, and oral products provided herein can be porous. When mixing liquid nicotine with cellulosic fiber, nicotine can become absorbed into the pores in the cellulosic fiber and held there by physical absorption (van der Waals forces). The number, sizes, size distribution, chemical, and physical properties of the pores can impact the release rate of nicotine incorporated into cellulosic fiber and into an oral product. The release rate can also be manipulated due to compressions cellulosic fiber (e.g., by chewing the oral product).

Methods for stabilizing nicotine provided herein can include mixing liquid nicotine with cellulosic fiber such that the liquid nicotine absorbs into pores of the cellulosic fiber to form a cellulosic fiber-nicotine mixture. In some cases, the liquid nicotine can include at least 1 weight percent nicotine. In some cases, the liquid nicotine can include between 2 weight percent and 75 weight percent nicotine and at least one diluent. In some cases, the diluent is selected from the group consisting of plasticizers, humectants, flavorants, or a combination thereof. A method provided herein can include diluting liquid nicotine with a diluent prior to mixing the liquid nicotine with cellulosic fiber. A method provided herein can include allowing the cellulosic fiber-nicotine mixture to equilibrate within a sealed container for at least 1 hour. In some cases, cellulosic fiber used in a method provided herein can include pores having an average pore size of between about 3 nanometers and about 300 nanometers. In some cases, a ratio of liquid nicotine to cellulosic fiber by weight in the cellulosic fiber-nicotine mixture is between 1/1000 and 50/50.

Methods for making an oral product provided herein can include mixing liquid nicotine with cellulosic fiber to produce a cellulosic fiber-nicotine mixture, mixing the cellulosic fiber-nicotine mixture with one or more binders to form an oral product pre-molding mixture, and molding the oral product pre-molding mixture into an oral product having a binder matrix, cellulosic fiber within the matrix, and nicotine within pores of the cellulosic fiber. The cellulosic fiber-nicotine mixture can be made using the processes and constituents provided herein. For example, liquid nicotine can be diluted with propylene glycol to a concentration of between 5% and 25% nicotine prior to mixing the liquid nicotine with the cellulosic fiber to form the cellulosic fiber-nicotine mixture. In some cases, a ratio of liquid nicotine to cellulosic fiber by weight in the cellulosic fiber-nicotine mixture is between 1/1000 and 50/50. In some cases, the binder includes a polymer. In some cases, the binder includes a water-soluble polymer. In some cases, the binder includes a mouth-stable polymer. In some cases, the binder includes a chewing gum base. In some cases, the binder is selected from the group consisting of dextrin or dextrin derivative, carboxymethyl cellulose, hydroxypropyl cellulose, hydroxyethyl cellulose, hydroxypropyl methyl cellulose, methyl cellulose, starch, konjac, collagen, inulin, soy protein, whey protein, casein, wheat gluten, carrageenan, alginates, propylene glycol alginate, xanthan, dextrin, pullulan, curdlan, gellan, locust bean gum, guar gum, tara gum, gum tragacanth, pectin, agar, zein, karaya, gelatin, psyllium seed, chitin, chitosan, gum acacia, polyvinyl pyrrolidone, polyethylene oxide, polyvinyl alcohol, guar gum, xanthan, cellulose, maltodextrin or other modified starch, polyurethane, silicon polymer, polyester, polyacrylate, polyethylene, poly(styrene-ethylene-butylene-styrene) ("SEBS"), poly(styrene-butadiene-styrene) ("SBS"), poly(styrene-isoprene-styrene)("SIS"), couma macrocarpa, loquat, tunu, jelutong, chicle, styrene-butadiene rubber, butyl rubber, and polyisobutylene, glycerol esters of gum, terpene resins, polyvinyl acetate, paraffin, microcrystalline wax, hydrogenated vegetable oils, lecithin, glycerol monosterate, natural latexes, chicle, spruce gum, mastic gum, or a combination thereof. In some cases, molding the oral product pre-molding mixture into the oral product includes compression molding the oral product pre-molding mixture into a predetermined shape. In some cases, molding the oral product pre-molding mixture into the oral product includes extruding and cutting the oral product pre-molding mixture into a predetermined shape. In some cases, molding the oral product pre-molding mixture into the oral product includes injection molding the oral product pre-molding mixture into a predetermined shape. In some cases, the oral product pre-molding mixture includes a dry mixture of ingredients. In some cases, the oral product pre-molding mixture is substantially free of ion-exchange resins. In some cases, the oral product pre-molding mixture is substantially free of buffering agents.

An oral product provided herein can include a mixture of cellulosic fiber and liquid nicotine where the liquid nicotine is absorbed into pores of the cellulosic fiber. In some cases, the oral product includes a binder holding the mixture of cellulosic fiber and liquid nicotine together into a solid piece. In oral product provided herein can have a predetermined shape. In some cases, the predetermined shape is formed by one or more of the processes provided herein. The binder(s) in the oral product provided herein can be the binders provided herein. The mixture of cellulosic fiber and liquid nicotine can be the cellulosic fiber-nicotine mixtures provided herein. In some cases, oral products provided herein can include a container. In some cases, an oral product provided herein can include a loose mixture of cellulosic fiber and liquid nicotine deposited within a container.

The details of one or more embodiments are set forth in the accompanying drawings and the description below. Other features and advantages will be apparent from the description and drawings, and from the claims.

DESCRIPTION OF DRAWINGS

FIG. 1 is a flow chart depicting an example of how liquid nicotine can be combined with cellulosic fiber and molded into an oral product.

DETAILED DESCRIPTION

This document provides methods and systems related to stabilizing liquid nicotine, incorporating liquid nicotine into an oral product, and providing an oral product having desirable nicotine-release characteristics. Liquid nicotine can be stabilized by mixing liquid nicotine with cellulosic fiber such that the liquid nicotine absorbs into pores of the cellulosic fiber to form a cellulosic fiber-nicotine mixture. An oral product can be manufactured by mixing a cellulosic fiber-nicotine mixture provided herein with one or more binders to form an oral product pre-molding mixture and molding the oral product pre-molding mixture into an oral product. Combining liquid nicotine with cellulosic fiber as provided herein can provide stabilized nicotine that can be used in a wide variety of molding operations, including compression molding techniques that call for dry ingredients. An oral product provided herein can have desirable nicotine-release characteristics.

Nicotine

Liquid nicotine used in cellulosic fiber-nicotine mixture provided herein can be tobacco-derived nicotine, synthetic nicotine, or a combination thereof. Liquid nicotine can be purchased from commercial sources, whether tobacco-derived or synthetic. Tobacco-derived nicotine can include one or more other tobacco organoleptic components other than nicotine. The tobacco-derived nicotine can be extracted from raw (e.g., green leaf) tobacco and/or processed tobacco. Processed tobaccos can include fermented and unfermented tobaccos, dark air-cured, dark fire cured, burley, flue cured, and cigar filler or wrapper, as well as the products from the whole leaf stemming operation. The tobacco can also be conditioned by heating, sweating and/or pasteurizing steps as described in U.S. Publication Nos. 2004/0118422 or 2005/0178398. Fermenting typically is characterized by high initial moisture content, heat generation, and a 10 to 20% loss of dry weight. See, e.g., U.S. Pat. Nos. 4,528,993; 4,660,577; 4,848,373; and 5,372,149. By processing the tobacco prior to extracting nicotine and other organoleptic components, the tobacco-derived nicotine may include ingredients that provide a favorable experience. The tobacco-derived nicotine can be obtained by mixing cured and fermented tobacco with water or another solvent (e.g., ethanol) followed by removing the insoluble tobacco material. The tobacco extract may be further concentrated or purified. In some cases, select tobacco constituents can be removed. Nicotine can also be extracted from tobacco in the methods described in the following patents: U.S. Pat. Nos. 2,162,738; 3,139,436; 3,396,735; 4,153,063; 4,448,208; and 5,487,792.

Liquid nicotine can be pure, substantially pure, or diluted prior to combination with cellulosic fiber. A diluting step shown in FIG. 1 is optional. In some cases, liquid nicotine is diluted to a concentration of between 1 weight percent and 75 weight percent prior to mixing the liquid nicotine with the cellulosic fiber. In some cases, liquid nicotine is diluted to a concentration of between 2 weight percent and 50 weight percent prior to mixing the liquid nicotine with the cellulosic fiber. In some cases, liquid nicotine is diluted to a concentration of between 5 weight percent and 25 weight percent prior to mixing the liquid nicotine with the cellulosic fiber. For example, liquid nicotine can be diluted to a concentration of about 10 weight percent prior to mixing the liquid nicotine with the cellulosic fiber.

In some cases, an oral product including a cellulosic fiber-nicotine mixture provided herein can include between 0.1 mg and 6.0 mg of liquid nicotine. In some cases, an oral product including a cellulosic fiber-nicotine mixture provided herein includes between 1.0 mg and 3.0 mg of liquid nicotine.

Diluent

As shown in FIG. 1, the liquid nicotine can be diluted prior to mixing the liquid nicotine with the cellulosic fiber. Liquid nicotine can be diluted with any suitable diluent. Diluting the liquid nicotine can provide more liquid volume for the liquid nicotine to help meter a precise amount of nicotine. Diluents can also facilitate absorption of nicotine into cellulosic fiber. In some cases, the diluent can be one or more plasticizers, one or more humectants, one or more flavorants, or a combination thereof. In some cases, a single substance can serve as both a plasticizer and a humectant, both a humectant and a flavorant, both a plasticizer and a flavorant, or as all three. For example, propylene glycol can serve as both a plasticizer and a humectant. For example, honey can serve as both a humectant and a flavorant. In some cases, the diluent can include a solvent (e.g., ethanol, water, etc.). In some cases, ethanol can be used as a diluent. Ethanol can act as a solvent, but also provide some plasticizing characteristics in the methods, systems, and products provided herein. In some cases, the diluent can include a sweetener. In some cases, the diluent can include a combination of plasticizers, humectants, solvents, sweeteners, and/or flavorants such that the cellulosic fiber-nicotine mixture mimics the flavor profile and tactile experience of certain tobacco products.

Suitable plasticizers include propylene glycol, glycerin, vegetable oil, partially hydrogenated vegetable oil, and medium chain triglycerides. In some cases, the plasticizer can include phthalates. Esters of polycarboxylic acids with linear or branched aliphatic alcohols of moderate chain length can also be used as plasticizers. In addition to serving as a diluent, plasticizers can facilitate the molding processes described below. Plasticizers can, in some cases, soften an oral product. In some cases, an oral product can include up to 20 weight percent plasticizer. In some cases, an oral product includes between 0.5 and 10 weight percent plasticizer, between 1 and 8 weight percent plasticizer, or between 2 and 4 weight percent plasticizer. For example, an oral product can include about 3 to 6.5 weight percent of propylene glycol.

A humectant is a substance that is used to keep things moist. Humectants can be hygroscopic. Suitable humectants include propylene glycol, hexylene glycol, butylene glycol, glyceryl triacetate, vinyl alcohol, neoagarobiose, sugar polyols (such as glycerol, sorbitol (E420), xylitol, maltitol, mannitol, and isomalt), polymeric polyols (e.g., polydextrose), quillaia, alpha hydroxyl acids (e.g., lactic acid), glycerin, aloe vera gel, and honey.

Flavorants can be natural or artificial. Flavorants can be selected from the following: licorice, wintergreen, cherry and berry type flavorants, Drambuie, bourbon, scotch, whiskey, spearmint, peppermint, lavender, cinnamon, cardamom, *Apium graveolens*, clove, cascarilla, nutmeg, sandalwood, bergamot, geranium, honey essence, rose oil, vanilla, lemon oil, orange oil, Japanese mint, cassia, caraway, cognac, jasmine, chamomile, menthol, ylang-ylang, sage, fennel, pimento, ginger, anise, coriander, coffee, mint oils from a species of the genus *Mentha*, cocoa, and combinations thereof. Synthetic flavorants can also be used. In certain embodiments, a combination of flavorants can be combined to imitate a tobacco flavor. The particular combination of flavorants can be selected from the flavorants that are generally recognized as safe ("GRAS").

A variety of synthetic and/or natural sweeteners can be used as in the diluent or added separately to an oral product. Suitable natural sweeteners include sugars, for example, monosaccharides, disaccharides, and/or polysaccharide sugars, and/or mixtures of two or more sugars. In some cases, a diluent can include one or more of the following: sucrose or table sugar; honey or a mixture of low molecular weight sugars not including sucrose; glucose or grape sugar or corn sugar or dextrose; molasses; corn sweetener; corn syrup or glucose syrup; fructose or fruit sugar; lactose or milk sugar; maltose or malt sugar or maltobiose; sorghum syrup; mannitol or manna sugar; sorbitol or d-sorbite or d-sobitol; fruit juice concentrate; and/or mixtures or blends of one or more of these ingredients. Diluent can, in some cases, include non-nutritive sweeteners. Suitable non-nutritive sweeteners include: stevia, saccharin; aspartame; sucralose; or acesulfame potassium.

Cellulosic Fiber

Cellulosic fiber used in the methods, systems, and oral products provided herein can be derived from plant tissue. In some cases, cellulosic fiber used in the methods, systems, and oral products provided herein can include cellulose. Cellulosic fiber used in the methods, systems, and oral products provided herein can further include lignin and/or lipids. Suitable sources for cellulosic fibers include wood pulp, cotton, sugar beets, bran, citrus pulp fiber, switch grass and other grasses, *Salix* (willow), tea, and *Populus* (poplar), bamboo. In some cases, cellulosic fiber used in the methods, systems, and oral products provided herein can be chopped or shredded plant tissue comprising various natural flavors, sweeteners, or active ingredients. Cellulosic fiber used in the methods, systems, and oral products provided herein can include a plurality of fibers having a variety of dimensions. In some cases, cellulosic fiber used in the methods, systems, and oral products provided herein can include one or more cellulosic fibers that are generally recognized as safe ("GRAS") for human consumption.

The dimensions of the cellulosic fibers (in addition to the amount) can impact the release characteristics of liquid nicotine from the mixture and from an oral product provided herein. The release profile of nicotine from an oral product can be impacted by both the fiber sizes, type and the amounts of cellulosic fiber. In some cases, the cellulosic fiber can be processed to have an average fiber size of less than 200 micrometers. In some cases, the fibers can be between 75 and 125 micrometers. In other embodiments, the fibers are processed to have a size of 75 micrometers or less. Cellulosic fiber can be hydrophilic, thus water soluble additives (e.g., nicotine) can preferentially be absorbed into pores of the cellulosic fiber.

Cellulosic fiber used in the methods, systems, and oral products provided herein can have pores. In some cases, cellulosic fibers provided herein have a pores sizes that range from between 3 nanometers to 300 nanometers. In some cases, cellulosic fibers provided herein have a pores sizes that range from between 10 nanometers to 200 nanometers. In some cases, cellulosic fibers provided herein have a pores sizes that range from between 20 nanometers to 100 nanometers. When mixing liquid nicotine with cellulosic fibers, nicotine can become absorbed into the pores in the cellulosic fibers and held there by van der Waals forces. The number, sizes, and size distribution, chemical, and physical surface properties of the pores can impact the release rate of nicotine incorporated into cellulosic fiber and into an oral product. The release rate can also be manipulated due to compression of cellulosic fiber (e.g., by chewing the oral product). The hydrophilicity of the cellulose fibers can be selected to provide a desired sensorial experience when included in an oral product. For example, cellulosic fiber can be hydrophilic, thus water soluble additives (e.g., nicotine) can preferentially be absorbed in cellulosic fiber.

Mixing and Equilibrating

As show in FIG. 1, cellulosic fiber and liquid nicotine are mixed and equilibrated. The cellulosic fiber and liquid nicotine can be mixed in a suitable mixing device for any suitable length of time. In some cases, the cellulosic fiber and liquid nicotine can be mixed with a mixing implement rotating at a speed of less than 500 rpm, less than 250 rpm, less than 150 rpm, less than 100 rpm, less than 60 rpm, less than 30 rpm, or less than 10 rpm. For example, the mixer can be a Kitchenaid, Hobart Mixe, ribbon blender, or other mixing apparatus depending on the desired batch size. In some cases, the cellulosic fiber and liquid nicotine can be mixed using a rotating and/or vibrating drum. In some cases, the cellulosic fibers and liquid nicotine can be mixed for at least 1 minute, at least 3 minutes, at least 5 minutes, at least 10 minutes, or at least 30 minutes prior to incorporating a resulting cellulosic fiber-nicotine mixture into an oral product.

After mixing cellulosic fiber and liquid nicotine, the cellulosic fiber-nicotine mixture can be equilibrated in a sealed container. In some cases, the sealed container can be a bag (e.g., a poly bag). In some cases, the cellulosic fiber-nicotine mixture can be equilibrated for at least 30 minutes, at least 1 hour, at least 2 hours, at least 4 hours, at least 6 hours, at least 8 hours, or at least 10 hours prior to use or incorporation into an oral product. In some cases, a cellulosic fiber-nicotine mixture can be further mixed or agitated during the equilibrating process. For example, a cellulosic fiber-nicotine mixture equilibrating in a poly bag can be agitated during the equilibrating process at a select time (e.g., 2 hours into the equilibrating process).

Oral Products

A cellulosic fiber-nicotine mixture provided herein can be combined with other ingredients and/or packaging to make an oral product. In some cases, an oral product provided herein can include a packaged quantity of a loose cellulosic fiber-nicotine mixture. In some cases, an oral product provided herein can include a quantity of cellulosic fiber-nicotine mixture within a porous pouch. In some cases, an oral product provided herein can include a molded body including at least one binder and a cellulosic fiber-nicotine mixture.

Cellulosic fiber-nicotine mixtures provided herein can be used to stabilize liquid nicotine for incorporation into an oral product. In some cases, an oral product provided herein can be produced by compression molding an oral product pre-molding mixture formed by mixing at least one or more binders and a cellulosic fiber-nicotine mixture provided herein. The oral product pre-molding mixture can be produced by compression molding a dry mixture. A dry mixture, as the term is used herein, means that the components are introduced to the molding apparatus in a solid form, as opposed to a liquid or melted form. Dry ingredients, for example, can include cellulosic fiber having absorbed nicotine, sugar alcohols, gums, maltodextrin, polysaccharides, sweeteners, flavors, and/or antioxidants. In some cases, the oral product pre-molding mixture can be sintered to form an oral product. In some cases, the oral product pre-molding mixture can be injection molded to form an oral product. In some cases, the oral product pre-molding mixture can be extruded and cut to form one or more oral products.

An oral product provided herein can further include one or more flavorants, sweeteners, humectants, and/or plasticizers, such as the flavorants, sweeteners, humectants, and plasticizers discussed above. As noted above, flavorants, sweeteners, humectants, and/or plasticizers can be added to the liquid nicotine to dilute the liquid nicotine. In some cases, flavorants, sweeteners, humectants, and/or plasticizers can be added to a cellulosic fiber-nicotine mixture provided herein after nicotine is absorbed. In some cases, flavorants, sweeteners, humectants, and/or plasticizers can be mixed with binder and a cellulosic fiber-nicotine mixture provided herein to form an oral product pre-molding mixture. Oral products provided herein can also include antioxidants and/or colorants.

The body of the oral product can have a variety of different shapes, some of which include disk, shield, rectangle, and square. According to certain embodiments, the body can have a length or width of between 5 mm and 100 mm and a thickness of between 1 mm and 30 mm.

Binder

The binder can be any suitable material that can hold a quantity of a cellulosic fiber-nicotine mixture provided herein together as a single piece.

In some cases, the binder can be a water-soluble polymer such that a resulting oral product can dissolve in an adult consumer's mouth. For example, the binder can be a carbohydrate. In some cases, the binder includes a hydroxyl containing compound, a dextrin or dextrin derivative, carboxymethyl cellulose, hydroxypropyl cellulose, hydroxyethyl cellulose, hydroxypropyl methyl cellulose, methyl cellulose, starch, konjac, collagen, inulin, soy protein, whey protein, casein, wheat gluten, carrageenan, alginates, propylene glycol alginate, xanthan, dextrin, pullulan, curdlan, gellan, locust bean gum, guar gum, tara gum, gum tragacanth, pectin, agar, zein, karaya, gelatin, psyllium seed, chitin, chitosan, gum acacia, polyvinyl pyrrolidone, polyethylene oxide, polyvinyl alcohol, or a combination thereof. In some cases, the binder is selected from the group of guar gum, xanthan, cellulose, and combinations thereof. In some cases, the binder can include maltodextrin or other modified starches.

In some cases, the binder can be a mouth-stable polymer. Suitable mouth-stable polymer matrix can include polyurethane, silicon polymer, polyester, polyacrylate, polyethylene, poly(styrene-ethylene-butylene-styrene) ("SEBS"), poly(styrene-butadiene-styrene) ("SBS"), poly(styrene-isoprene-styrene)("SIS"), and other similar thermoplastic elastomers, or any copolymer, mixture, or combination thereof.

In some cases, the binder can be a chewing gum base. A chewing gum base can include ingredients from the following categories: elastomers (such as couma macrocarpa, loquat, tunu, jelutong, chicle, styrene-butadiene rubber, butyl rubber, and polyisobutylene); resins (such as glycerol esters of gum, terpene resins, and/or polyvinyl acetate); waxes (such as paraffin or microcrystalline wax); fats (such as hydrogenated vegetable oils); emulsifiers (such as lecithin or glycerol monosterate); fillers (such as calcium carbonate or talc); antioxidants (e.g., BHT, BHA, tocopherol, ascorbyl palmitate). In some cases, a chewing gum base can include natural latexes, vegetable gums (e.g., chicle), spruce gum, and/or mastic gum.

A number of embodiments of the invention have been described. Nevertheless, it will be understood that various modifications may be made without departing from the spirit and scope of the invention. Accordingly, other embodiments are within the scope of the following claims.

What is claimed is:

1. An oral product comprising:
a mixture including,
   a cellulosic material, the cellulosic material including wood pulp, cotton, sugar beet, bran, citrus pulp fiber, switch grass, grass, *Salix*, tea, *Populus*, bamboo fiber, or any combinations thereof, and
   diluted nicotine absorbed into pores of the cellulosic material, the diluted nicotine including,
      nicotine, and
      a diluent including a medium chain triglyceride.

2. The oral product of claim 1, wherein the nicotine includes tobacco-derived nicotine.

3. The oral product of claim 1, wherein the nicotine includes synthetic nicotine.

4. The oral product of claim 1, wherein a weight ratio of the cellulosic material to the diluted nicotine ranges from 1:1000 to 50:50.

5. The oral product of claim 1, wherein the nicotine is present in the oral product in an amount ranging from 0.1 mg to 6.0 mg.

6. The oral product of claim 1, wherein the nicotine is present in the diluted nicotine in an amount greater than or equal to 1 weight percent.

7. The oral product of claim 6, wherein the nicotine is present in the diluted nicotine in an amount ranging from 2 weight percent to 75 weight percent.

8. The oral product of claim 1, wherein the medium chain triglyceride is present in the oral product in an amount less than or equal to 20 weight percent.

9. The oral product of claim 8, wherein the medium chain triglyceride is present in the oral product in an amount ranging from 2 weight percent to 4 weight percent.

10. The oral product of claim 8, wherein the medium chain triglyceride is present in the oral product in an amount ranging from 3 weight percent to 6.5 weight percent.

11. The oral product of claim 1, wherein the pores have an average pore size ranging from 3 nanometers to 300 nanometers.

12. The oral product of claim 1, further comprising:
a sweetener.

13. The oral product of claim 12, wherein the sweetener includes a natural sweetener including a monosaccharide, a disaccharide, a polysaccharide, or any combination thereof.

14. The oral product of claim 12, wherein the sweetener includes sucrose, honey, glucose, molasses, corn sweetener, corn syrup, fructose, lactose, maltose, sorghum syrup, mannitol, sorbitol, fruit juice concentrate, stevia, saccharin, aspartame, sucralose, acesulfame potassium, or any combination thereof.

15. The oral product of claim 1, further comprising:
a humectant.

16. The oral product of claim 15, wherein the humectant includes propylene glycol, hexylene glycol, butylene glycol, glyceryl triacetate, vinyl alcohol, neoagarobiose, a sugar polyol, a polymeric polyol, quillaia, an alpha hydroxyl acid, glycerin, aloe vera gel, honey, or any combination thereof.

17. The oral product of claim 1, further comprising:
a flavorant.

18. The oral product of claim 17, wherein the flavorant includes licorice, wintergreen, cherry, a berry type flavorant, Drambuie, bourbon, scotch, whiskey, spearmint, peppermint, lavender, cinnamon, cardamom, *Apium graveolens*, clove, cascarilla, nutmeg, sandalwood, bergamot, geranium, honey essence, rose oil, vanilla, lemon oil, orange oil, Japanese mint, cassia, caraway, cognac, jasmine, chamomile, menthol, ylang-ylang, sage, fennel, pimento, ginger, anise, coriander, coffee, mint oils from a species of the genus *Mentha*, cocoa, or any combination thereof.

19. The oral product of claim 1, wherein the cellulosic material includes cellulosic fibers having a size ranging from 75 micrometers to 125 micrometers.

20. The oral product of claim 1, further comprising:
a container, the mixture being within the container.

* * * * *